United States Patent [19]

Karaki et al.

[11] Patent Number: 4,977,779
[45] Date of Patent: Dec. 18, 1990

[54] ULTRASONIC MICROSCOPE HAVING A FOCUSING MECHANISM

[75] Inventors: Koichi Karaki, Hino; Mitsugu Sakai; Yasuo Sasaki, both of Hachiooji, all of Japan

[73] Assignee: Olympus Optical Co., Ltd., Tokyo, Japan

[21] Appl. No.: 381,136

[22] Filed: Jul. 14, 1989

[30] Foreign Application Priority Data

Jul. 21, 1988 [JP] Japan ................................ 63-182679

[51] Int. Cl.$^5$ .............................................. G01N 29/00
[52] U.S. Cl. ........................................ 73/606; 73/620
[58] Field of Search ................. 73/606, 633, 634, 642, 73/618, 619, 620

[56] References Cited

FOREIGN PATENT DOCUMENTS

| 58-72052 | 4/1983 | Japan ..................................... | 73/606 |
| 58-196453 | 11/1983 | Japan . | |
| 59-44582 | 10/1984 | Japan . | |
| 63-154961 | 6/1988 | Japan ..................................... | 73/606 |

OTHER PUBLICATIONS

The Journal of Acoustic Society of America, vol. 67 (May, 1980), pp. 1629-1637—J. Heiserman et al., "Cryogenic Acoustic Microscopy".

D. Ruger et al., "Acoustic Microscopy at Temperaturess less than 0.2° K.," *Acoustical Imaging*, vol. 12 (1982), pp. 13-25.

*Primary Examiner*—John Chapman
*Attorney, Agent, or Firm*—Frishauf, Holtz, Goodman & Woodward

[57] ABSTRACT

An ultrasonic microscope includes a housing for containing a cryogenic liquid. A sample support mechanism is secured to a frame inside the housing, and an acoustic lens located in the housing in the cryogenic liquid applies an ultrasonic beam to the sample supported by the support mechanism. A voice coil device suported by the frame operates to move the sample support mechanism in response to a drive current, and to fix a distance between the acoustic lens and the sample. A control arrangement associated with the voice coil device generates an EMF in response to movement of the support mechanism, and supplies a current caused by the EMF to the drive circuit wherein movement of the support mechanism is controlled by the current to maintain the sample at a desired position with respect to the acoustic lens.

9 Claims, 2 Drawing Sheets

ULTRASONIC MICROSCOPE HAVING A FOCUSING MECHANISM

BACKGROUND OF THE INVENTION

1. Field of the Invention

The present invention relates to an ultrasonic microscope having a focusing mechanism and using a cryogenic fluid as a medium for transmission of an ultrasonic beam.

2. Description of the Related Art

Japanese Patent Publication No. 59-44582 and Japanese Patent Disclosure No. 58-196453 disclose ultrasonic microscopes in which a sample is two-dimensionally scanned with an ultrasonic beam, and the waves passing through, or reflected from, the sample are processed to form an image of the sample.

In these microscopes, the ultrasonic beam must be focused onto the sample in order to form a clear image of the sample. To achieve a successful focusing of the beam, it is necessary to adjust, with high accuracy, the distance between beam-focusing means, e.g., an acoustic lens, and a surface or an internal plane of the sample, thus setting this distance within the focal depth of the microscope. *The Journal of Acoustic Society of America*, Vol. 67 (1980), pp. 1629-37, discloses a cryogenic ultrasonic microscope which can provide a high-resolution ultrasonic image of a sample. To conduct the ultrasonic beam from the acoustic lens to the sample efficiently, a beam-transmitting medium is filled in the gap between the acoustic lens and the sample. The beam transmitting medium is cryogenic liquid such as liquid nitrogen, liquid argon, or liquid helium, which transmits sound more slowly and absorbs less than water.

The cryogenic ultrasonic microscope also has a focusing mechanism. The mechanism is located outside the housing containing the cryogenic liquid. Due to the position of the focusing mechanism, the microscope as a whole is complex in structure, and heat can easily propagate into the housing. Hence, the temperature of the cryogenic liquid is likely to rise, making it impossible to accomplish high-accuracy focusing of the ultrasonic beam.

SUMMARY OF THE INVENTION

Accordingly, the object of the present invention is to provide an ultrasonic microscope which has a simple structure, uses a cryogenic liquid as beam-transmitting medium, and can achieve high-accuracy focusing of an ultrasonic beam.

DETAILED DESCRIPTION OF THE PREFERRED EMBODIMENTS

Figure 1:
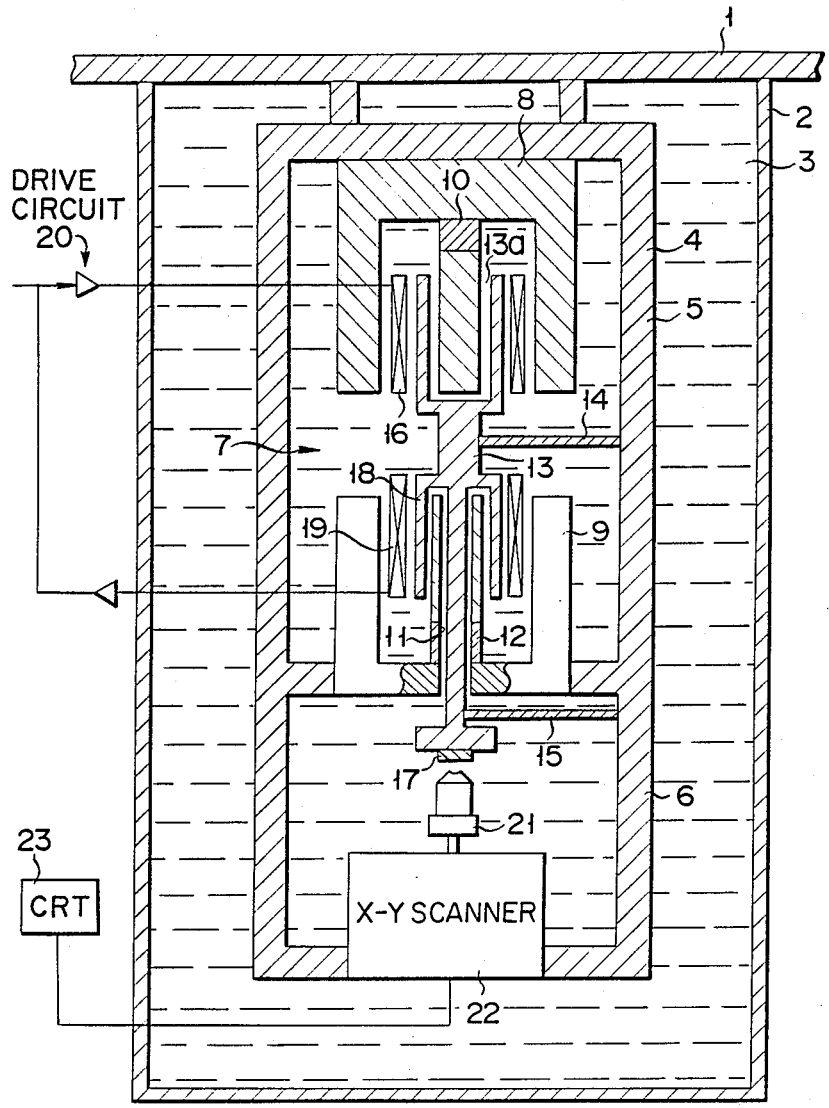
FIG. 1 is a sectional view illustrating an ultrasonic microscope according to the present invention.

An ultrasonic microscope, which is an embodiment of the invention, will now be described with reference to FIG. 1. As is shown in this Figure, the microscope comprises a support plate 1 and a housing or adiabatic vessel 2 removably secured to the plate 1, with its opening closed by the plate 1. The vessel 2 is sealed in airtight fashion from the support plate 1, and no heat can propagate from outside into the adiabatic vessel 2. The adiabatic vessel 2 is almost completely filled with cryogenic liquid 3 such as liquid nitrogen or liquid helium, which is used as medium for transmitting an ultrasonic beam.

The adiabatic vessel 2 contains a frame unit 4 which is immersed in the cryogenic liquid 3. The frame unit 4 is formed of an upper frame 5 and a lower frame 6, both being rectangular. The unit 4 is, as a whole, rectangular, extending in vertical direction. As is evident from FIG. 1, the frame unit 4 is suspended from the support plate 1. Alternatively, the unit 4 can be mounted on, and secured to, the bottom of the adiabatic vessel 2. Further, the unit can be a hollow cylinder as a whole.

A focusing mechanism 7 (i.e., a voice-coil mechanism) is held within the upper frame 5. This mechanism 7 has two yokes 8 and 9. The upper yoke 8 and the lower yoke 9 are fastened to the upper and lower horizontal plates of the upper frame 5, respectively. The upper yoke 8 has three arms extending downward, parallel to one another. A permanent magnet 10 is embedded in the proximal portion of the center arm. The lower yoke 9 also has three arms extending upward, parallel to one another. These three arms are opposite to the three arms of the upper yoke 8. The center arm of the lower yoke 9 has a vertical guide hole 11 extending through the lower yoke 9. A hollow cylindrical permanent magnet 12 is embedded in the lower yoke 9 and located coaxial with the guide hole 11. The left and right arms of either yoke can be continuous to each other in a horizontal plane, thus forming, for example, a hollow cylinder.

A movable shaft 13 is located vertically within the frame unit 4. The shaft 13 is supported by two leaf springs 14 and 15 connected to the inner side of the frame unit 4, and can move up and down. The shaft 13 includes a hollow cylindrical upper portion, an intermediate portion, and a thin lower portion.

The center arm of the upper yoke 8 is loosely inserted in the upper portion 13a of the movable shaft 13. An upper coil 16 is wound around the upper portion 13a of the shaft 13. The coil 16 is electrically connected to a drive circuit 20 located outside the adiabatic vessel 2 and having a DC-power source. When a current is supplied from the circuit 20 to the upper coil 16, the coil 16 generates a magnetic field. This magnetic field cooperates with the magnetic field of the permanent magnet 10, to move the shaft 13 up or down against the bias of the leaf springs 14 and 15, for a distance proportional to the amount of the current flowing through the upper coil 16.

The lower portion of the movable shaft 13 extends via the vertical guide hole 11 into the lower frame 6. A sample 17 is attached to the tip of this lower end portion. A hollow cylinder 18 is coaxially secured to the intermediate portion of the movable shaft 13, and surrounds the center arm of the lower yoke 9, which in turn surrounds the lower end portion of the shaft 13. A lower coil 19 is wound around the cylinder 18. The lower coil 19 cooperates with the magnetic field of the permanent magnet 12, to generate an electrical current when the shaft 13 moves up or down. This current is proportional to he speed at which the shaft 13 moves. The lower coil 19 is connected to the input of the drive circuit 20. Therefore, the current generated by the lower coil 19 is supplied to the drive circuit 20. As a result of this, the circuit 20 controls the current supplied to the upper coil 16 in accordance with the current the coil 19 has generated, thereby to stop the movable shaft 13. In other words, the lower coil 19 locks the shaft 13 at the position to which the shaft 13 has been moved by means of the upper coil 16.

The lower frame 6 contains an acoustic lens 21 which comprises a piezoelectric transducer (not shown). The acoustic lens 21 is attached to the upper end of an X-Y scanner 22 which is secured to the lower frame 6. The X-Y scanner 22 is positioned such that the lens 21 is spaced apart from the sample 17 by a predetermined distance. The cryogenic liquid 3 fills the gap between the sample 17 and the acoustic lens 21. The acoustic lens 21 is of a known type. It applies an ultrasonic beam to the sample 17, receives the waves reflected from the sample 17 and converts these waves into electrical signals representing the intensities of the waves. The X-Y scanner 22 can move in a horizontal plane, in an x-direction and a y-direction. Hence, the acoustic lens 21 can also move in a horizontal plane, thereby to scan the sample 17 with the ultrasonic beam.

The X-Y scanner 22, which has such a structure as is shown in the mentioned Journal of Acoustic Society of America article, can serve to position the two-dimensional plane of the acoustic lens 21 parallel to the surface of the sample 17. More specifically, it moves in the x-direction and the y-direction, thus moving the lens 21 in the horizontal plane, and detects the values of the V (Z) signals generated when the lens 21 is located at several positions with respect to the sample 17. Based on observation of the V(Z) signals on an oscilloscope CRT 23, an operator can adjust the drive circuit 20 to move the focusing mechanism 7 until the V (Z) signals come to have the same value, thus indicating that the two-dimensional plane of the lens 21 is parallel to the surface of the sample 17.

The CRT (Cathode Ray Tube) 23 is connected through scanner 22 to the output of the acoustic lens 21, for displaying the wave form of the voltage output by the acoustic lens 21. This voltage is the highest when the ultrasonic beam is focused on the surface of the sample 17. Therefore, an operator turns a dial connected to a variable resistor (not shown), thus changing the current input from the drive circuit 20 to the upper coil 16, up until the waveform of the voltage display on the CRT 23 has the highest peak.

Figure 2:
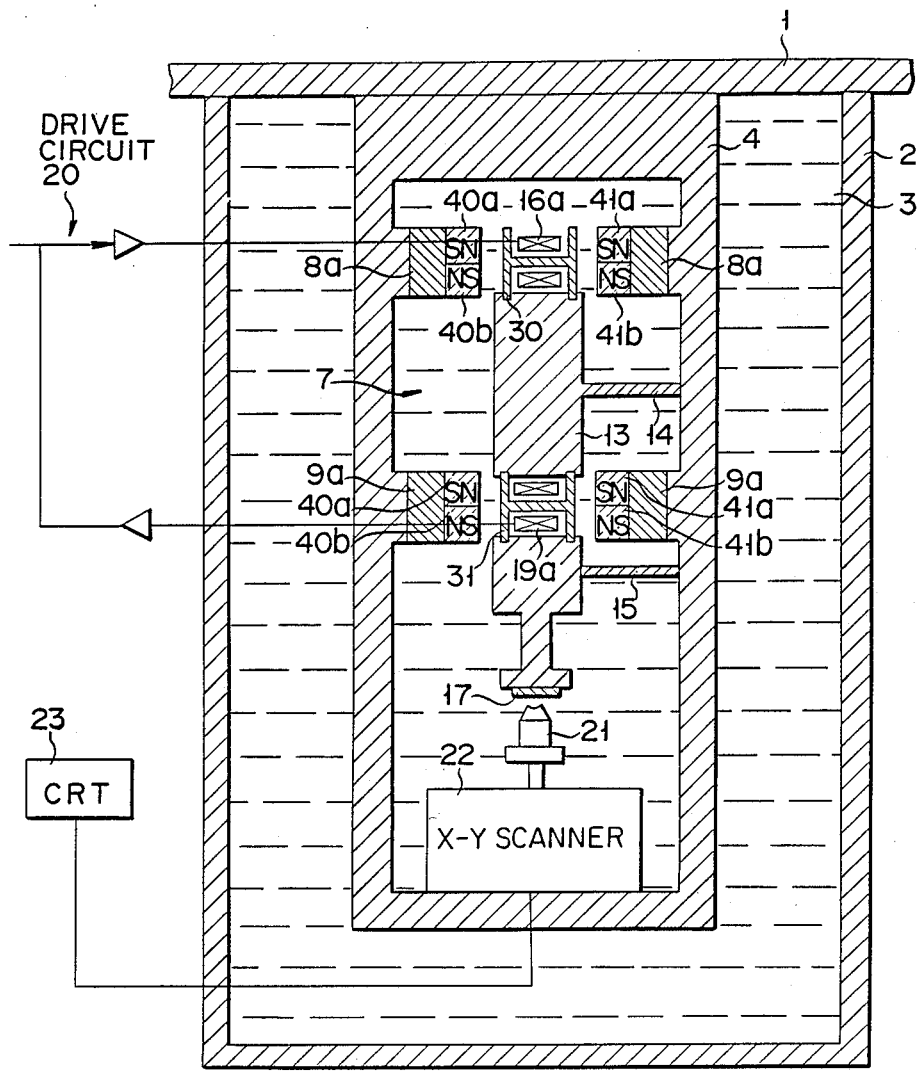
FIG. 2 is a sectional view showing another ultrasonic microscope according to this invention.

FIG. 2 illustrates a second embodiment of the present invention, which is identical to the first embodiment (FIG. 1), except for the focusing mechanism. The focusing mechanism 7 used in the second embodiment has two bobbins 30 and 31 made of non-magnetic material and connected to the upper end and middle portion of a movable shaft 13, respectively. An upper coil 16a is wound around the bobbin 30 which extends horizontally. Similarly, a lower coil 19a is wound around the bobbin 31 which extends horizontally.

Two yokes 8a and 9a are fastened to the inner surface of a rectangular frame 4 and surround the bobbins 30 and 31, respectively. A pair of permanent magnets 40a and 41a are attached to the yokes 8a, opposing the ends of the upper coil 16a. A pair of permanent magnets 40b and 41b are attached to the yoke 8a in a similar manner. The magnets 40a and 41b are positioned with their N poles facing the S poles of the magnets 41a and 40b. Hence, a magnetic flux passes through the upper coil 16a from the magnet 40a to the magnet 41a, and another magnetic flux passes through the coil 16a from the magnet 41b to the magnet 40b.

Further, a pair of permanent magnets 40a and 41a, and a pair of magnets 40b and 41b are attached to the yokes 9a and oppose the ends of the lower coil 19a. Two magnetic fluxes pass through the coil 19a in the opposite directions between the magnets 40a and 40b, on the one hand, and the magnets 41a and 41b, on the other. When an electrical current is supplied to the upper coil 16a, the coil 16a generates a magnetic field. This magnetic field and the magnetic fluxes of the magnets 40a, 40b, 41a, and 41b cause the shaft 13 to move vertically against the leaf springs 14 and 15, for the distance proportional to the amount of the current supplied to the upper coil 16a.

The lower coil 19a is used to lock the shaft 13 at the position to which the shaft 13 has been moved vertically, as in the first embodiment illustrated in FIG. 1. The X-Y scanner of the second embodiment (FIG. 2) is identical in structure with its counterpart of the first embodiment.

In either embodiment described above, the acoustic lens, the sample, the focusing mechanism, and the X-Y scanner are located within the same frame. Both the focusing mechanism and the X-Y scanner, for adjusting the positional relationship between the acoustic lens and the sample, can be remote-controlled in accordance with electrical signals externally supplied. Furthermore, the frame is entirely immersed in the cryogenic liquid. Hence, no heat can propagate into the frame to raise the temperature of the liquid. Therefore, the ultrasonic beam can be accurately focused on the sample.

The coils, used in either embodiment as means for moving the shaft supporting the sample, generate heat while electrical currents are flowing through them. In view of this, it is desirable that these coils be made of superconductive wires.

What is claimed is:

1. An ultrasonic microscope, comprising:
   a housing for containing a cryogenic liquid;
   a frame provided within said housing;
   support means secured to said frame, for supporting a sample so that the sample is immersed in the cryogenic liquid;
   an acoustic lens located within the housing and immersed in the cryogenic liquid, for applying an ultrasonic beam to the sample supported by said support means;
   a scanner for causing said acoustic lens to scan the sample two-dimensionally;
   a voice coil device supported by said frame, for moving said support means in response to a drive current, and for fixing a distance between said acoustic lens and the sample;
   a drive circuit for supplying a drive current to said voice coil device; and
   control means associated with said voice coil device for generating an electromotive force (EMF) in response to movement of said support means, and for supplying a current caused by said EMF to said drive circuit, wherein the movement of said support means is controlled by said current to maintain the sample at a desired position with respect to said acoustic lens.

2. The ultrasonic microscope according to claim 1, wherein said frame has a lower frame having a horizontal plate and containing said acoustic lens and said scanner, and an upper frame having a horizontal plate and supporting said voice coil device; and said support means has a shaft extending from said upper frame into said lower frame and having a hollow cylindrical portion and a lower end for supporting the sample, and elastic means connecting said shaft to said frame, allowing said shaft to move in a vertical direction.

3. The ultrasonic microscope according to claim 2, wherein said voice-coil device has:
- an upper yoke having a center arm and two side arms, which extend in the vertical direction, the upper yoke fixed on the horizontal plate, and the center arm loosely inserted in the hollow cylindrical portion of said support means;
- an upper magnet fixed to the proximal end of the center arm of said upper yoke and generating a magnetic field between said center arm and said side arms;
- a coil provided around said hollow cylindrical portion of said shaft, for generating a magnetic field; and
- said drive circuit supplying a current to said coil whereby the shaft is vibrated in the vertical direction by the cooperation of the magnetic fields generated by the upper magnet and coil.

4. The ultrasonic microscope according to claim 3, wherein said control means has:
- a lower yoke fixed to the upper frame, and having three arms extending toward the arms of said upper yoke, respectively;
- a guide hole formed in the center arm of said lower yoke and guiding said shaft;
- a lower magnet fixed on the center arm of said lower yoke, said lower magnet being a hollow cylinder coaxial with said guide hole of said center arm of said lower yoke;
- a coil for generating electromotive force, being provided around the center arm of the lower yoke and fixed on the shaft; and
- a device for supplying a current to said drive circuit, said current, generated,,when said shaft is vibrated, from the coil of the control means.

5. The ultrasonic microscope according to claim 2, wherein said voice-coil device has:
- an upper yoke having a center arm fastened to said horizontal plate of said upper frame and extending in the vertical direction, and a hollow cylinder surrounding the center arm;
- an upper magnet fixed to said upper yoke, for generating a magnetic field in the space between said center yoke and said hollow cylinder;
- a coil provided around said hollow cylindrical portion of said shaft, for generating a magnetic field; and
- said drive circuit for supplying a current to said coil whereby the shaft is vibrated in the vertical direction by the cooperation of the magnetic fields generated by the upper magnet and the coil.

6. The ultrasonic microscope according to claim 2, wherein said voice-coil device comprises:
- first and second voice-coils;
- the first voice-coil including a first coil for moving the shaft in a vertical direction and said drive circuit for supplying a current to the first coil;
- the second voice-coil including a lower yoke having a center arm fastened to the upper frame and extending in the vertical direction, and a hollow cylinder surrounding the center arm;
- a guide hole made in the center arm of said lower yoke and guiding said shaft;
- a lower magnet fixed to said lower yoke, for generating a magnetic field in the space between said center yoke and said hollow cylinder, said lower magnet being a hollow cylinder coaxial with said guide hole of the center arm of said lower yoke;
- a second coil for generating electromotive force, said second coil being provided around a hollow cylinder connected to an intermediate portion of said shaft, and spaced apart from said shaft for a predetermined distance; and
- a device for supplying a current to said drive circuit, said current generated, when said shaft is vibrated, from the magnetic field generated in a space between the center arm and the hollow cylinder of said lower yoke.

7. The ultrasonic microscope according to claim 1, wherein said frame contains said acoustic lens and said scanner in a lower portion; and said support means has a shaft extending vertically through said frame and having an end, for supporting the sample, and elastic means connecting said shaft to said frame, allowing said shaft to move in a vertical direction.

8. The ultrasonic microscope according to claim 7, wherein said voice-coil device has a coil provided on said shaft, for generating a magnetic field; said drive circuit supplying a current to said coil; and magnetic means for vibrating said shaft in the vertical direction by utilizing the magnetic field generated by said coil, said magnetic means having magnets connected to both sides of said frame by means of yokes.

9. The ultrasonic microscope according to claim 8, wherein said control means has a coil provided on said shaft for generating electromotive force, and a device for supplying a current to said drive circuit, said current being generated from the coil of said control means when said shaft is vibrated.

* * * * *